(12) United States Patent
Haggerty (10) Patent No.: US 8,950,252 B2
(45) Date of Patent: Feb. 10, 2015

(54) HIGH PRESSURE ROCK CORE TESTING

(75) Inventor: Dennis J. Haggerty, Burleson, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 13/814,931

(22) PCT Filed: Apr. 20, 2012

(86) PCT No.: PCT/US2012/034568
§ 371 (c)(1),
(2), (4) Date: Feb. 7, 2013

(87) PCT Pub. No.: WO2013/158120
PCT Pub. Date: Oct. 24, 2013

(65) Prior Publication Data
US 2014/0007667 A1    Jan. 9, 2014

(51) Int. Cl.
*G01N 15/08* (2006.01)
*G01N 33/24* (2006.01)
*G01N 15/00* (2006.01)
*E21B 49/00* (2006.01)

(52) U.S. Cl.
CPC .............. *G01N 33/241* (2013.01); *G01N 15/00* (2013.01); *G01N 15/082* (2013.01); *E21B 49/00* (2013.01)
USPC ...................................................... 73/152.07

(58) Field of Classification Search
CPC ......................... G01N 15/0826; G01N 15/082
USPC .............................. 73/152.07, 152.09, 152.11
See application file for complete search history.

(56) References Cited

U.S. PATENT DOCUMENTS

| | | | |
|---|---|---|---|
| 4,253,327 A | 3/1981 | Wiley | |
| 4,552,011 A * | 11/1985 | Wiley | 73/1.69 |
| 4,555,934 A | 12/1985 | Freeman et al. | |
| 4,561,289 A * | 12/1985 | Jones | 73/38 |
| 4,573,342 A * | 3/1986 | Jones | 73/38 |
| 4,643,019 A * | 2/1987 | Jones | 73/38 |
| 4,884,438 A | 12/1989 | Jones et al. | |
| 5,263,360 A * | 11/1993 | Blauch et al. | 73/38 |
| 5,265,462 A * | 11/1993 | Blauch et al. | 73/38 |
| 5,503,001 A * | 4/1996 | Wong | 73/38 |
| 5,677,478 A * | 10/1997 | Murphy, Jr. | 73/38 |
| 8,043,998 B2 * | 10/2011 | Pope et al. | 507/205 |
| 8,549,905 B2 * | 10/2013 | Brooks et al. | 73/152.07 |
| 8,683,858 B2 * | 4/2014 | Piri | 73/152.06 |
| 2010/0137169 A1 * | 6/2010 | Pope et al. | 507/205 |
| 2011/0271751 A1 | 11/2011 | Brooks et al. | |
| 2013/0031969 A1 * | 2/2013 | Brooks et al. | 73/152.07 |

OTHER PUBLICATIONS

Haggerty Dennis J., PCT Application entitled, "High Pressure Rock Core Testing", filed on Apr. 20, 2012, Int'l Application PCT/US2012/034568.
Foreign Communication—International Search Report and Written Opinion, PCT/US2012/034568 dated Dec. 26, 2012.

* cited by examiner

*Primary Examiner* — John Fitzgerald
(74) *Attorney, Agent, or Firm* — Chamberlain Hrdlicka (57) ABSTRACT

A rock core flow test system comprises a first high pressure accumulator, a second high pressure accumulator, and a fast opening flow control device coupled to a wellbore facing end of the rock core. The fast opening flow control device opens when a pressure differential across the flow control device exceeds a predetermined threshold. The first high pressure accumulator is coupled to at least one of a pore end of the rock core and a radial surface of the rock core. The second high pressure accumulator is coupled to the fast opening flow control device. The system further comprises a pressure sensor coupled to the rock core flow test system between the fast opening flow control device and the second high pressure accumulator.

20 Claims, 7 Drawing Sheets

HIGH PRESSURE ROCK CORE TESTING

CROSS-REFERENCE TO RELATED APPLICATIONS

This application claims priority under 35 U.S.C. §371 and is a National stage of International Application No. PCT/US2012/034568, entitled "High Pressure Rock Core Testing", by Dennis Haggerty, filed Apr. 20, 2012 in the United States Receiving Office, which is incorporated herein by reference in its entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Hydrocarbons may be produced from wellbores drilled from the surface through a variety of producing and non-producing formations. The wellbore may be drilled substantially vertically or may be an offset well that is not vertical and has some amount of horizontal displacement from the surface entry point. In some cases, a multilateral well may be drilled comprising a plurality of wellbores drilled off of a main wellbore, each of which may be referred to as a lateral wellbore. Portions of lateral wellbores may be substantially horizontal to the surface. In some provinces, wellbores may be very deep, for example extending more than 10,000 feet from the surface.

A variety of servicing operations may be performed on a wellbore after it has been initially drilled. A lateral junction may be set in the wellbore at the intersection of two lateral wellbores and/or at the intersection of a lateral wellbore with the main wellbore. A casing string may be set and cemented in the wellbore. A liner may be hung in the casing string. The casing string may be perforated by firing a perforation gun or perforation tool. A packer may be set and a formation proximate to the wellbore may be hydraulically fractured. A plug may be set in the wellbore.

Perforation tools may comprise explosive charges that are detonated to fire the perforation tool, perforate a casing if present, and create perforations and/or tunnels into a subterranean formation proximate to the wellbore. The tunnels into the subterranean formation may be surrounded by an envelope or layer of crushed material. The crushed material may shift and/or flow into the tunnels, clogging the tunnels to some extent, reducing the ease with which hydrocarbons can flow from the subterranean formation, through the perforations in the casing, and up the wellbore. Additionally, metal material in the perforation gun, such as a portion of a tool body of the perforation gun proximate to the explosive charges and/or a charge liner may be deposited in the tunnels, potentially partially clogging the tunnels. On net, it is desired that perforation not only opens the casing to allow hydrocarbons to flow into the wellbore but further increases the flow rate of hydrocarbons relative to what would have been the flow rate if the casing was merely opened without creating tunnels in the subterranean formation. As indicated above, however, the flow rate of hydrocarbons may be increased or decreased relative to the flow rate that would theoretically be experienced by a tunnel-less subterranean formation as a result of the perforation. A variety of perforation tool design parameters can be adjusted with the intention of encouraging desired results and mitigating undesired results of the perforation. A density of shots into the subterranean formation can be adjusted. An angle of the focus axis of the explosive charges can be adjusted to angle up, to angle down, or to angle normal to the axis of the perforation tool, though an angle normal to the axis of the perforation tool may provide the greatest degree of penetration of the formation. Parameters of the explosive charge itself may be altered to adapt to different downhole parameters including the shape of the charge, the amount of explosive material, the construction of a explosive charge liner, a design of the perforation gun tool body proximate to the explosive charges, and other parameters.

Sometimes downhole perforation procedures are conducted with pre-firing wellbore pressure maintained below the formation fluid pressure, which may be referred to as an under balanced condition, or maintained above the formation fluid pressure, which may be referred to as an over balanced condition. Sometimes a tool may be carried with the perforation tool or incorporated into the perforation tool to create a transient fluid surge after firing of the perforation tool to supplement or prolong an under balanced condition. The perforation procedure may be designed to adapt to different perforation conditions based on estimations and/or projections of downhole parameters. For example, a pre-firing wellbore pressure may be calculated to provide a specific intensity of under balance or over balance. In the case an under balance condition is desired, a volume of fluid surge may be calculated.

In order to design the perforation tool and/or a downhole perforation procedure, one or more rock cores that are considered to be representative of the subterranean formation to be perforated may be tested to determine some parameters of the subterranean formation and/or interactions between the explosive charges and the subterranean formation. The evaluations of test results may be used in designing the perforation tool and/or the downhole perforation procedure.

SUMMARY

In an embodiment, a rock core flow test system is disclosed. The rock core flow test system comprises a first high pressure accumulator, a second high pressure accumulator, and a fast opening flow control device coupled to a wellbore facing end of the rock core. The fast opening flow control device opens when a pressure differential across the flow control device exceeds a predetermined threshold. The first high pressure accumulator is coupled to at least one of a pore end of the rock core and a radial surface of the rock core. The second high pressure accumulator is coupled to the fast opening flow control device. The system further comprises a pressure sensor coupled to the rock core flow test system between the fast opening flow control device and the second high pressure accumulator.

In an embodiment, a method of performing a rock core flow performance test is disclosed. The method comprises increasing a pressure applied to at least one of a pore end of the rock core or a radial surface of the rock core to a first pressure, wherein the first pressure is greater than about 15,000 pounds per square inch (PSI), measuring the pressure on a wellbore facing axial end of the rock core to determine a time interval over which the measured pressure drops from a second pressure to a third pressure, and determining a high pressure production ratio of the rock core based on the time interval.

In an embodiment, a method of performing a rock core flow performance test is disclosed. The method comprises increasing a pressure applied to a formation axial end of the rock core to a first pressure, wherein the first pressure is greater than about 15,000 pounds per square inch (PSI) and increasing a pressure applied to a wellbore axial end of the rock core to the first pressure, wherein the increasing pressure applied to the formation axial end of the rock core and the increasing pressure applied to the wellbore axial end of the rock core are maintained substantially equal as the pressures increase to the first pressure. The method further comprises, while maintaining the pressure applied to the formation axial end of the rock core at the first pressure, reducing the pressure applied to the wellbore axial end of the rock core until a fast opening flow control device activates, wherein the fast opening flow control device activates in response to a threshold pressure differential across the fast opening flow control device, capturing an overflow of a fluid that flows through the rock core after the activation of the fast opening flow control device, weighing the overflow of the fluid that flows through the rock core, and, based on a weight of the overflow of the fluid, determining a first flow volume of the fluid through the rock core.

In an embodiment, a method of performing a rock core flow performance test is disclosed. The method comprises increasing a pressure applied to at least one of a pore end of the rock core or a radial surface of the rock core to a first pressure, wherein the first pressure is greater than about 15,000 pounds per square inch (PSI) and increasing a pressure applied to a wellbore facing side of a fast opening flow control device to the first pressure, wherein the increasing pressure applied to the pore end of the rock core or to the radial surface of the rock core and the increasing pressure applied to the wellbore facing side of the fast opening flow control device are maintained substantially equal as the pressures increase to the first pressure, wherein a core facing side of the fast opening flow control device is coupled to a wellbore facing end of the rock core. The method further comprises, while maintaining the pressure applied to the pore end of the rock core or the radial surface of the rock core at the first pressure, reducing the pressure applied to the wellbore facing side of the fast opening flow control device until the fast opening flow control device activates at a second pressure; measuring the pressure on the wellbore facing side of the fast opening flow control device to determine a first time interval over which the measured pressure drops from the second pressure to a third pressure; and determining a high pressure production ratio of the rock core based on the first time interval.

In an embodiment, a rock core flow test system is disclosed. The system comprises a first high pressure accumulator, a second high pressure accumulator, and a fast opening high pressure flow control device that opens when a pressure differential across the flow control device exceeds a predetermined threshold. The system further comprises an overburden rock core high pressure containment vessel coupled between the first high pressure accumulator and the fast opening high pressure flow control device, wherein the fast opening high pressure flow control device is coupled between the overburden rock core high pressure containment vessel and the second high pressure accumulator, a pressure sensor coupled to the rock core flow test system between the fast opening high pressure flow control device and the second high pressure accumulator, and a high speed pressure logging device coupled to the pressure sensor.

In an embodiment, a method of performing a rock core flow performance test is disclosed. The method comprises increasing a pressure applied to a formation axial end of the rock core to a first pressure, wherein the first pressure is greater than about 15,000 pounds per square inch (PSI) and increasing a pressure applied to a wellbore axial end of the rock core to the first pressure, wherein the increasing pressure applied to the formation axial end of the rock core and the increasing pressure applied to the wellbore axial end of the rock core are maintained substantially equal as the pressures increase to the first pressure. The method further comprises, while maintaining the pressure applied to the formation axial end of the rock core at the first pressure, reducing the pressure applied to the wellbore axial end of the rock core until a fast opening flow control device activates, wherein the fast opening flow control device activates in response to a threshold pressure differential across the fast opening flow control device, capturing an overflow of a fluid that flows through the rock core after the activation of the fast opening flow control device, weighing the overflow of the fluid that flows through the rock core, and, based on a weight of the overflow of the fluid, determining a first flow volume of the fluid through the rock core.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents.

Unless otherwise specified, any use of any form of the terms "connect," "engage," "couple," "attach," or any other term describing an interaction between elements is not meant to limit the interaction to direct interaction between the elements and may also include indirect interaction between the elements described. Reference to up or down will be made for purposes of description with "up," "upper," "upward," or "upstream" meaning toward the surface of the wellbore and with "down," "lower," "downward," or "downstream" meaning toward the terminal end of the well, regardless of the wellbore orientation. The term "zone" or "pay zone" as used herein refers to separate parts of the wellbore designated for treatment or production and may refer to an entire hydrocarbon formation or separate portions of a single formation such as horizontally and/or vertically spaced portions of the same formation. The various characteristics mentioned above, as well as other features and characteristics described in more detail below, will be readily apparent to those skilled in the art with the aid of this disclosure upon reading the following detailed description of the embodiments, and by referring to the accompanying drawings.

Testing of rock cores may be conducted to evaluate and to adjust perforation gun design parameters and perforation procedure parameters. Testing may be conducted based on American Petroleum Institute (API) reference procedure 19B (API RP 19B), *Recommended Practices for Evaluation of Well Perforators*, First Edition, November 2000. Testing is typically performed on a rock core that is considered to be representative of the subterranean formation. For example, rock cuttings from a subterranean formation retrieved from the wellbore to be perforated are captured and analyzed to determine characteristics of the rock of the subterranean formation. An outcrop rock is selected based on the similarity of its characteristics to the characteristics of the rock cuttings from the subterranean formation. The outcrop rock is trimmed to a form suitable for core testing, for example a circular cylinder form about 7 inches in diameter and about 28 inches in axial length. The length of the rock core may be a different length, depending on the perforation tunnel depth expected to be produced by the perforation charge. In some cases a core sample may be extracted from the wellbore and used in rock core testing, but such core samples are expensive to obtain and are less and less frequently available.

The present disclosure contemplates performing at least some of the core testing using high pressure conditions that may be seen in some downhole environments. This high pressure core testing presents design challenges. In an embodiment, the rock core is flow tested under high pressure without perforation; during a simulated perforation event, the rock core is flow tested under high pressure after perforation; and a metric is calculated relating rock core flow before and after perforation to determine if the perforation improved the flow. If the perforation did not improve the flow, the perforation gun design may be adapted accordingly. The metric can also be used to compare among a plurality of different perforation gun designs to select the perforation gun design that performs best in the rock core test. In an embodiment, evaluation of flow results are based on pressure sensed at a wellbore axial face of the rock core rather than directly sensing fluid flow rate.

The rock core may be placed in a containment or pressure vessel that is sealed at one end by a fast opening flow control device, for example by a rupture disc. In some contexts, the fast opening flow control device may be referred to as a high speed flow control device. The rock core may be disposed within a sleeve or bladder and an external surface of the sleeve or bladder may be subjected to a high overburden pressure or confining pressure along at least a portion of its surface (e.g., along its radial surface), for example an overburden pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI. The application of the pressure to a sleeve or bladder may be referred to as an indirect pressure based on the lack of any direct contact between the fluid exerting the overburden pressure and the rock core. The overburden pressure or confining pressure may be viewed as simulating the pressure experienced in the downhole environment.

A subterranean formation axial end or pore axial end of the rock core may be subjected to a fluid having a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI but less than the overburden pressure or confining pressure. In some contexts the pressure applied to the pore axial end of the rock core may be referred to as the flow pressure based on the direct contact between the fluid and the rock core. The wellbore facing end of the fast opening flow control device may be subjected to a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI but less than the overburden pressure. The pressure on the pore axial end of the rock core and the pressure on the wellbore facing end of the fast opening flow control device may be increased in unison so that they remain substantially equal up to a first pressure. In an embodiment, a distributor may be employed to provide the pressure and flow to the pore axial end of the rock core. In an embodiment, the distributor may have a floating design that promotes applying the same pressure to both the pore axial end of the rock core and to the radial surface of the rock core.

The first pressure is maintained at the pore axial end of the rock core while the pressure on the wellbore facing side of the fast opening flow control device is decreased until a pressure difference between the pressure on the pore axial end of the rock core and the pressure on the wellbore facing end of the fast opening flow control device exceed a predefined threshold, for example a pressure differential of about 2,000 PSI. It is understood that when the fast opening flow control device is closed (hence no fluid flow through the rock core), the pressure applied to the pore axial end of the rock core is equalized across the rock core, and the pressure applied to the pore axial end of the rock core is equal to the pressure applied to a core facing side of the fast opening flow control device. As the pressure differential exceeds the predefined threshold, the fast opening flow control device opens quickly, for example the rupture disc ruptures. The pressure on the wellbore facing side of the fast opening flow control device when the device activates or opens may be referred to as a second pressure. The second pressure is less than the first pressure. After the fast opening flow control device activates, the rock core experiences a flow, and the pressure at the wellbore facing side of the fast opening flow control device drops from the second pressure to a third pressure over a first time interval. In combination with the present disclosure, the first pressure, the second pressure, and the third pressure may be selected by one skilled in the art. In practice, the selection of the first pressure, the second pressure, and the third pressure may be based, at least in part, on available or conveniently manufactured fast opening flow control devices. The pressures may also be selected at least in part to simulate downhole conditions as nearly as is practicable.

After the non-perforated rock core test, a layer of cement that models casing cement is adhered to the wellbore facing axial end of the rock core. A layer of metal that models casing metal is adhered to the cement. The cement and layer of metal may be referred to as a target plate and/or a target faceplate.

An explosive charge is coupled to the metal layer with a gap between the metal layer and the explosive charge, where this gap models the gap between the perforation gun and the casing in a downhole environment. The explosive charge may comprise a shaped explosive, a charge liner, and a metal layer that models a tool body of a perforation gun proximate to the explosive charge. For example, the metal layer of the explosive charge may include a scalloped area. The metal layer of the explosive charge may model a gun wall material and thickness.

The rock core and this perforation assembly are placed in the containment. In this situation, the wellbore facing axial end of the rock core is sealed by the perforation assembly. The rock core is again indirectly exposed to high overburden pressure along at least a portion of its radial surface, for example an overburden pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI. The pore axial end of the rock core may be subjected to a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI but less than the overburden pressure.

The wellbore facing end of the perforation assembly may be directly subjected to a high pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI but less than the overburden pressure. The wellbore facing end of the perforation assembly may be directly subjected to a pressure substantially equal to the pressure at which the fast opening flow control device described above opened, for example to the second pressure described above.

The explosive charge is then fired, and the explosion creates a hole in the target faceplate and creates a tunnel into the rock core. As is known by one skilled in the art, the length of the rock core is sized to avoid the tunnel penetrating all the way through the rock core. The API RP 19B *Recommended Practices for Evaluation of Well Perforators*, identified above, recommends that the tunnel extend no further than a distance equal to the diameter from the pore end of the rock core. For example, if the rock core is 7 inches in diameter and 28 inches long, the tunnel caused by the explosion should penetrate no further than 21 inches into the rock core (and hence 7 inches from the pore end of the rock core). The rock core may be examined after the explosion and after the transient pressure test to determine if this recommendation has been satisfied, for example, a sonogram of the rock core after the explosion may be made using an ultrasonic analysis tool. If the explosion penetrates excessively into the rock core, a longer rock core may be formed and one or more of the tests may be repeated with the longer rock core.

After perforation, the rock core experiences a flow, and the pressure at the wellbore facing axial end of the rock core drops from the second pressure to the third pressure over a second time interval. The first and second time intervals can be compared to determine a production ratio that promotes an evaluation of the effectiveness of the explosive charge design for use with the rock core. In an embodiment, the volumetric flow of fluid through the rock core under high pressure may be determined by capturing overflow of fluids and weighing the fluid. Because under the high pressure conditions of the rock core testing the fluid may experience compression, the volumetric flow of fluid through the rock core may be determined by determining the uncompressed volume of the fluid based on the measured weight and then converting this uncompressed volume to a compressed volume based on known or determinable compressibility relationships of the subject fluid. Standard flow rate sensors may not be practicable in the high pressure test environment taught by the present disclosure, for example testing in an environment with pressures greater than about 25,000 PSI. In an embodiment, the rock core is flowed with odorless mineral spirits (ODM), but in another embodiment a different fluid may be flowed in the rock core. While the description above describes fluid flowing from the pore axial end to the wellbore axial end of the rock core, with substantially no flow across the radial axial surface of the rock core, in another embodiment, the core test procedure may be modified and fluid may flow across the radial axial surface of the rock core.

It is understood that in some embodiments, the test that employs a fast opening flow control device and be performed without the test that explodes an explosive charge. In some embodiments, the test that explodes an explosive charge may be performed without the test that employs the fast opening flow control device. In an embodiment, the two types of tests may be performed but using different rock cores. For example, the two types of tests may be performed on different rock cores at the same time. Alternatively, the test that explodes an explosive charge may be performed on a first rock core and then later the test that employs the fast opening flow control device may be performed on a second rock core.

Figure 1:
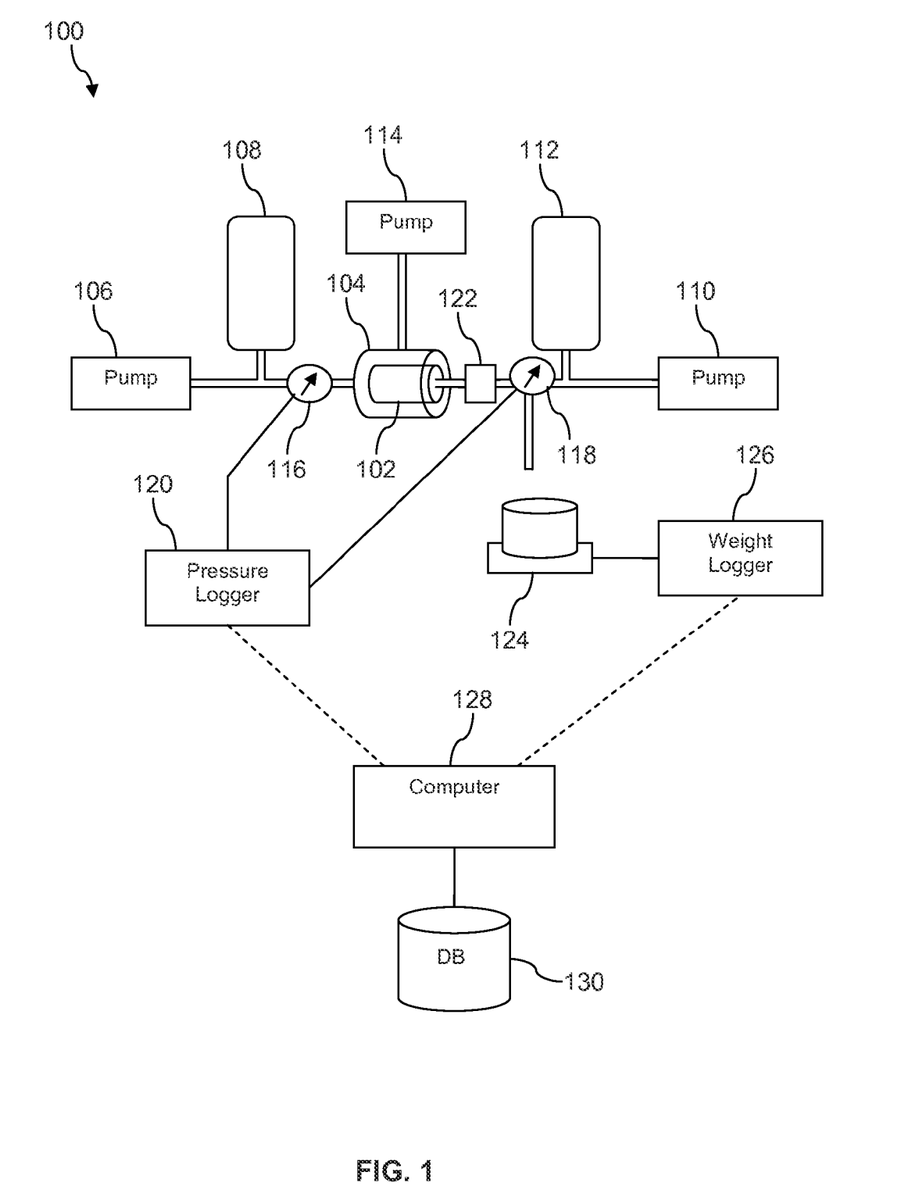
FIG. 1 is an illustration of a rock core testing system according to an embodiment of the disclosure.

Turning now to FIG. 1, a system 100 for testing a rock core is described. Testing a rock core may be referred to simply as core testing. In an embodiment, the system 100 comprises a rock core 102, a containment vessel 104, a first pump 106, a first high pressure accumulator 108, a second pump 110, a second high pressure accumulator 112, and a third pump 114. In an embodiment, the system 100 further comprises a first pressure sensor 116, a second pressure sensor 118, a high speed pressure logger 120, a fast opening high pressure flow control device 122, a scale 124, and a weight logger 126. In some contexts, the fast opening high pressure flow control device 122 may be referred to as a high speed high pressure flow control device. The pumps 106, 110, and 114 are capable of providing fluid at high pressure, for example fluid at pressure greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI. In an embodiment, the pumps 106, 110, and 114 may be capable of supplying fluid pressurized up to about 50,000 PSI. In an embodiment, the pumps 106, 110, and 114 may be triplex type pumps, but in another embodiment a different type of pump may be employed.

It is understood that the system 100 may contain components and equipment not explicitly described herein. For example, a flow distributor (not shown) may be used to couple between the rock core 102 and the first pump 106 and/or the first accumulator 108. High pressure piping may be used to couple components of the system 100 to each other. Check valves may be used to impose one-way flow directionality in some portions of the system 100. Pressure relief valves may be used to promote safety and/or to promote collecting fluid as an indication of fluid flow through the rock core 102.

The system 100 may promote maintaining a constant overburden pressure or confining pressure on the radial surface of the rock core 102 that is different from the pressure applied to the axial ends of the rock core 102, wherein fluid flow may occur across a pore axial end of the rock core 102 and fluid flow is substantially blocked across the radial surface of the rock core 102. In an embodiment, a sleeve or bladder surrounds the radial surface of the rock core 102 and prevents or attenuates fluid flow across the radial surface of the rock core 102. Pressure applied to the sleeve, for example overburden or confining pressure, is then applied to the radial surface of the rock core 102. Alternatively, in an embodiment, the system 100 may promote maintaining the same pressure on the pore axial end of the rock core 102 and on the radial surface of the rock core 102, wherein fluid flow may occur across both the pore axial end of the rock core 102 and across the radial surface of the rock core 102. Alternatively, in an embodiment, the system 100 may promote sealing the pore axial end of the rock core 102 and applying pressure to the radial surface of the rock core 102 and flowing fluid across the radial surface of the rock core 102. In some contexts, the rock core 102 may be referred to as a core sample. In other contexts, however, the term core sample may be reserved to distinguish a rock core that has been extracted from the specific subterranean formation and the wellbore for which a perforation gun is to be designed. In some contexts, the containment vessel 104 may be referred to as a pressure vessel.

The high pressure accumulators 108, 112 receive in-flow of fluid that is resisted by a chamber of the accumulators that is filled with a compressible substance such as nitrogen gas. The high pressure accumulators 108, 112 act to maintain an operating pressure by delivering fluid flow and receiving fluid flow to maintain pressure through fluid flow demand transients. One skilled in the art can be expected to be familiar with the principle of operation of such accumulators. It is to be noted that the high pressure accumulators 108, 112 are designed specifically for operating at high pressures above 25,000 PSI. The design characteristics of the high pressure accumulators 108, 112 that make them suitable for use in high pressure environments may include a strength of the accumulator vessel, a shape of the accumulator vessel, and an initial pressure of the compressible substance contained by the accumulator. For example, in an embodiment, the accumulator vessel may have a substantially spherical shape.

The fast opening high pressure flow control device 122 is designed to open rapidly when a pressure differential across the component exceeds a predefined threshold. For example, the predefined threshold may be about 500 PSI, about 1000 PSI, about 2000 PSI, or some other pressure differential. One of ordinary skill in the art will appreciate that individual fast opening flow control devices may manifest some unit-to-unit variation without nullifying the value of the tests. For example, a specific instance of a fast opening high pressure flow control device 122 designed to open in response to a pressure differential exceeding 500 PSI may in fact open when the pressure differential exceeds 450 PSI or may not open until the pressure differential exceeds 550 PSI. Generally, such unit-to-unit variation can be tolerated or this variation may be accommodated by post-test analysis of test data. Alternatively, if the unit-to-unit variation experienced during a core test is excessive, the subject test results may be discarded and the core testing may be repeated. It is understood that, in some embodiments, the fast opening high pressure flow control device 122 is designed for use in high pressure environments, for example, in environments with pressures greater than about 5,000 pounds per square inch (PSI), greater than about 10,000 PSI, greater than about 15,000 PSI, greater than about 20,000 PSI, greater than about 25,000 PSI, greater than about 30,000 PSI, greater than about 35,000 PSI, greater than about 40,000 PSI, greater than about 45,000 PSI, or greater than about 50,000 PSI. In some contexts, the fast opening high pressure flow control device 122 may be referred to as the fast opening flow control device 122 or the high speed flow control device 122.

For purposes of the present disclosure, fast opening means that the subject flow control device is substantially fully opened after a period of time that is small relative to the time interval used to determine the production ratio (to be discussed further hereinafter). For example, in an embodiment, after the onset of the opening of the fast opening flow control device 122, the fast opening flow control device 122 is at least 80% fully open before 20% of the time interval used to determine the production ratio. Alternatively, in an embodiment, after the onset of the opening of the fast opening flow control device 122, the fast opening flow control device 122 is at least 80% fully open before 10% of the time interval used to determine the production ratio.

Alternatively, the fast opening flow control device 122 may be substantially open in less than about 500 milliseconds (mS), less than about 300 mS, less than about 10 mS, less than about 5 mS, less than about 1 mS, less than about 100 microseconds (µS), less than about 50 µS, less than about 10 µS, less than about 5 µS, or less than about 1 µS. In an embodiment, the fast opening flow control device 122 may be a rupture disc. In another embodiment, the fast opening flow control device 122 may be a valve that is held closed by a shear pin or shear disc that fails predictably at a predefined pressure differential across the fast opening flow control device 122 and after failure undergoes rapid opening in response to the forcing of the pressure differential and an associated fluid flow. In another embodiment, a different form of valve may be used to provide the fast opening flow control device 122.

The high speed pressure logger 120 receives indications of pressure from the first pressure sensor 116 and from the second pressure sensor 118. In an embodiment, the high speed pressure logger 120 may filter the indications of pressure received from the pressure sensors 116, 118 to remove noise and/or other perturbations from the indications unrelated to the pressure. The high speed pressure logger 120 may record the received indications of pressure at a periodic rate of 1000 hertz, 10000 hertz, 100000 hertz, or some other periodic rate. The high speed pressure logger 120 may store each pressure sample as an entry in a file that represents the given pressure value and the time associated with the pressure value. In an embodiment, the high speed pressure logger 120 may capture up to about 625,000 sample values per second. In another embodiment, however, a different sampling rate may be provided by the high speed pressure logger 120. In an embodiment, different types of pressure measurements may be stored by the high speed pressure logger 120 comprising, for example, pressure transients stored at a very high sampling rate as well as static pressure data sampled and recorded about every 7.5 seconds before and after opening of the fast opening flow control device 122.

In an embodiment, the high speed pressure logger 120 may comprise a ballistic pressure gauge. The ballistic pressure gauge may generally be configured to measure a plurality of pressure readings based on an input signal. For example, the opening of the fast opening flow control device 122 (e.g., a rupture disk or perforating charge) may trigger the initiation of the pressure readings at the time of the input signal or after a short delay. In an embodiment, the ballistic pressure gauge may allow for up to about 50,000 readings, up to about 100,000 readings, up to about 150,000 readings, up to about 160,000 readings, or up to about 200,000 readings in a period ranging from about 0.001 seconds to about 1 second, about 0.01 seconds to about 0.75 seconds, or about 0.02 seconds to about 0.05 seconds. The ballistic pressure gauge may then be used to measure fluid flow of greater than about 50 ml/min, greater than about 75 ml/min, or greater than about 100 ml/min.

The scale 124 may comprise a receptacle to capture fluid overflow from the system 100, for example from a relief valve downstream of the fast opening flow control device 122. The receptacle is coupled to the scale 124 so that the weight of overflowed fluid may be weighed by the scale 124. In an embodiment, the receptacle may be releasably coupled to the scale 124, for example to promote draining fluid from the receptacle and cleaning the receptacle. The scale 124 may provide the indications of weight to the weight logger 126, and the weight logger 126 may filter the indications of weight received from the scale 124 to remove noise and/or other perturbations from the indications unrelated to weight. The weight logger 126 may record the received indications of weight at a periodic rate of 0.1 hertz, 0.5 hertz, 1 hertz, 2 hertz, 10 hertz, or some other periodic rate. The weight logger 126 may store each weight sample as an entry in a file that represents the given weight value and the time associated with the time value. In an embodiment, the weight logger 126 determines a tare weight output by the scale 124 when no fluid is contained by the receptacle coupled to the scale 124 and automatically compensates the weight indication received from the scale 124 based on the tare weight before creating records that are stored in the weight file.

In an embodiment, a computer 128 may receive pressure data from the pressure logger 120 and weight data from the weight logger 126. For example, the computer 128 may establish a wireless communication link or a wired communication link with the pressure logger 120 and down load the pressure versus time data entries to a data store 130. The computer 128 may concurrently or at a different time establish a wireless communication link or a wired communication link with the weight logger 126 and down load the weight versus time data entries to the data store 130. Alternatively, the pressure and weight data may be streamed to the computer 128 by the pressure logger 120 and the weight logger 126 substantially as the subject data is collected. The data store 130 may be a database, a flat file stored in memory or in secondary memory, a directory service such as a lightweight directory access protocol (LDAP) storage, or some other form of data store. The computer 128 may process the data received from the loggers 120, 126 in a variety of ways and may process the data associated with different separate sets of data captured during different stages of rock core testing.

Figure 2:
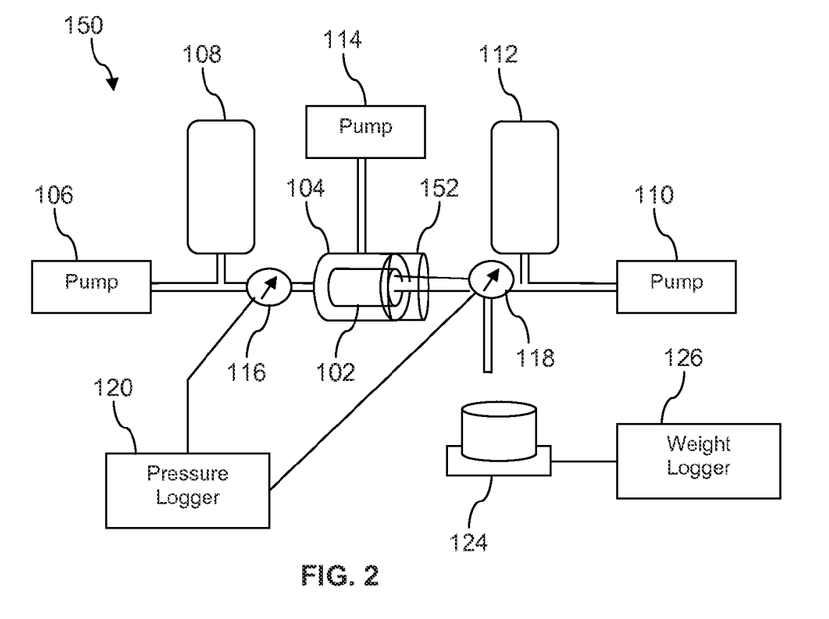
FIG. 2 is an illustration of a rock core testing system according to another embodiment of the disclosure.

Turning now to FIG. 2, a system 150 is described. System 150 is substantially similar to system 100 described above, but rather than the fast opening flow control device 122, system 150 comprises a perforation assembly 152. In an embodiment, system 100 is suitable for completing a first stage of rock core testing, and system 150 is suitable for completing a second stage of rock core testing, as described in more detail hereinafter.

Figure 3:
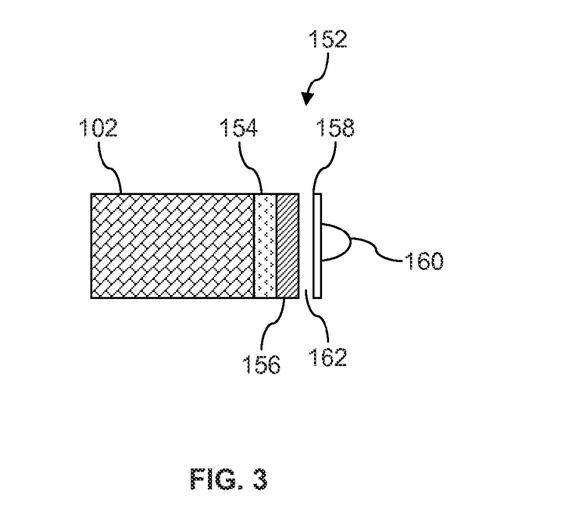
FIG. 3 is an illustration of a rock core prepared for use in a test procedure according to an embodiment of the disclosure.

Turning now to FIG. 3, the perforation assembly 152 is described. In an embodiment, the perforation assembly 152 comprises a target plate comprising a cement layer 154 and a metal layer 156 which are adhered to the wellbore facing axial end of the rock core 102 with the cement layer 154 proximate to the wellbore facing axial end of the rock core 102. An explosive charge 160 is coupled to a tool body metal plate 158. The tool body metal plate 158 is held in position to maintain a spacing gap 162 between the metal layer 156 of the target plate and the tool body metal plate 158. The explosive charge 160 may be aligned to focus its firing energy parallel to and desirably coincident with the central axis of the rock core 102.

The cement layer 154, the metal layer 156, the tool body metal plate 158, the explosive charge 160, and the spacing gap 162 are arranged to simulate as nearly as practicable the downhole conditions of perforating a subject wellbore. The cement layer 154 may be created to be similar to the cement provided to a wellbore to be perforated. The metal layer 156 may be selected to approximate the thickness and metal properties of a casing in the wellbore to be perforated. The tool body metal plate 158 may be formed of metal material and to have a thickness like that of a contemplated perforation gun tool body. The spacing gap 162 may be selected to approximate an expected gap between the planned perforation gun and the casing in the wellbore to be perforated. It is understood that different wellbores will be associated with different cement materials and different casing materials. Thus, the cement layer 154 and the metal layer 156 used for testing a rock core associated with a first wellbore may be different from the cement layer 154 and metal layer 156 used for testing a rock core associated with a second wellbore.

Figure 4:
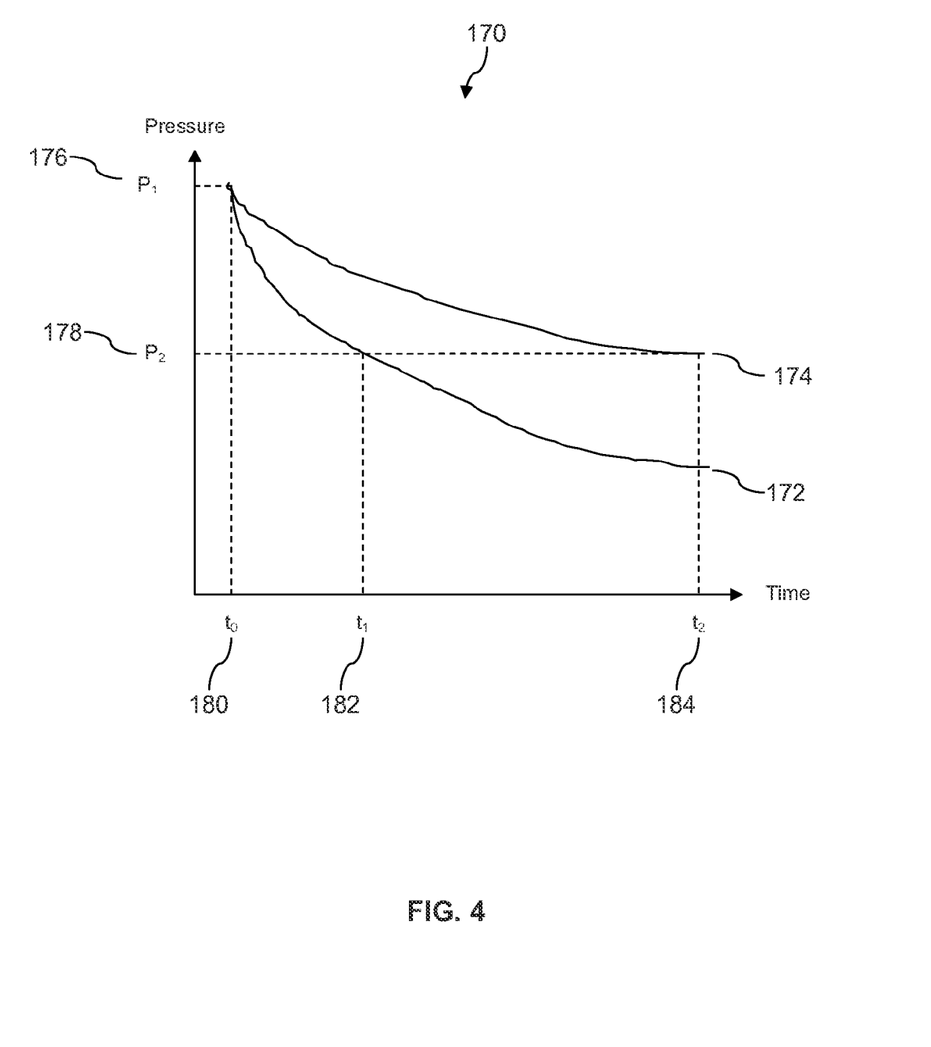
FIG. 4 is a curve illustrating exemplary test pressures according to an embodiment of the disclosure.

Turning now to FIG. 4, a plurality of pressure versus time curves 170 are described. The curves 170 represent at least some of the results of what may be referred to as a transient pressure test. Such a transient pressure test may be performed with equipment described above and using methods described further hereinafter. The transient pressure test may be employed in the presence of high pressures that may not be attainable in the steady-state flow tests heretofore used to test rock cores. In an embodiment, the transient pressure test may be used to determine a number of properties of the rock core 102, for example one or more of a production factor, permeability of the rock core 102 before and after perforation, surface area of the rock core 102 before and after perforation (after perforation, an equivalent wellbore axial end surface area may be determined for comparison to a known wellbore axial end surface area prior to perforation), production flow before and after perforation, skin damage from perforation, and other properties of the rock core 102 and/or of the simulated perforation design.

A first pressure versus time curve 172, referred to hereafter as the pressure curve 172, corresponds to testing flow in the rock core 102 without perforation, using the system 100 described above. A second pressure versus time curve 174, referred to hereafter as the pressure curve 174, corresponds to testing flow in the rock core 102 during and after the simulated perforation event, using system 150 described above. The pressure associated with the curves 170 is the pressure as sensed by the second pressure sensor 118, located on the wellbore side of the fast opening flow control device 122 in system 100 and on the wellbore side of the perforation assembly 152 in system 150. A first pressure 176 may be an initial pressure at which the rock core 102 is flow tested. A second pressure 178 may be an arbitrary reference pressure for completing test result analysis. In pressure curve 172, when the fast opening flow control device 122 opens, the pressure is initially sensed by the second pressure sensor 118 to be at the first pressure 176 and drops to the second pressure 178 over a time interval from the initial time 180 to the first end time 182. The difference between the initial time 180 and the first end time 182 may be referred to as a first time interval. In pressure curve 174, when the perforation assembly 152 is fired, the pressure is initially sensed by the second pressure sensor 118 to be at the first pressure 176 and drops to the second pressure 178 over a time interval from the initial time 180 to the second end time 184. The difference between the initial time 180 and the second end time 184 may be referred to as a second time interval.

The different time intervals over which the pressure sensed by the second pressure sensor 118 drops from the first pressure 176 to the second pressure 178 during the two stages of the rock core testing can give a relative indication of the effectiveness of the perforation gun design. A production ratio (PR) can be calculated as:

$$PR=[(P_1-P_2)/(t_1-t_0)]/[(P_1-P_2)/(t_2-t_0)] \qquad \text{Eq. 1A}$$

$$PR=(t_2-t_0)/(t_1-t_0) \qquad \text{Eq. 1B}$$

where $P_1$ is the first pressure 176, $P_2$ is the second pressure 178, $t_0$ is the initial time 180, $t_1$ is the first end time 180, and $t_2$ is the second end time 182. The pressure $P_2$ may be the final pressure for a simulated perforation event test. The time $t_1$ may be the time an open core test takes to achieve the pressure $P_2$. The $t_2$ may be the time the simulated perforation event test takes to achieve the pressure $P_2$. A production ratio greater than unity indicates that the modeled perforation gun design improves production of the subject rock core with reference to an unperforated rock core; a production ratio less than unity indicates the modeled perforation gun design reduces production of the subject rock core with referent to an unperforated rock core. Production ratios of different tests using different modeled perforation gun designs may be used to compare between different perforation gun designs. Thus, a first perforation gun design associated with a higher production ratio than the production ratio associated with a second perforation gun design suggests that the first perforation gun design can be expected to provide better production results from the subject wellbore. It is understood that the production ratio may also be determined in another way. For example, a value for the time interval $t_1-t_0$ associated with the high pressure test involving a fast opening flow control device may be estimated based on a low pressure flow test performed on the rock core or a similar rock core. Based on other tests, a mapping may be established between low pressure flow test results and the transient pressure test using the fast opening flow control device.

Figure 5:
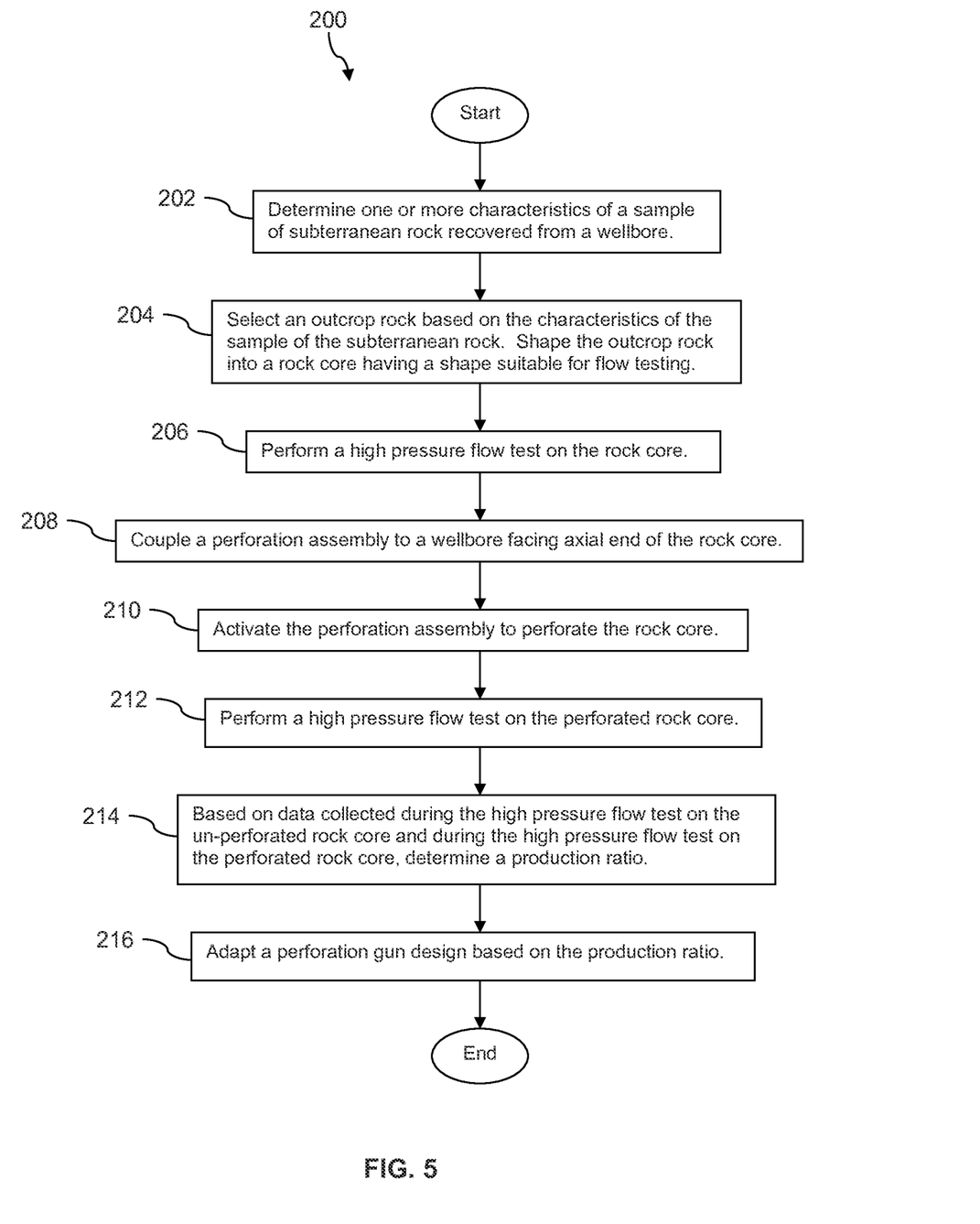
FIG. 5 is a flow chart of a method according to an embodiment of the disclosure.

Turning now to FIG. 5, a method 200 is described. In an embodiment, the method 200 may be employed to perform a transient pressure test. At block 202, one or more characteristics of a sample of subterranean rock recovered from the wellbore that is to be perforated are determined. The characteristics may be the density of the rock, the permeability of the rock, the type of rock, and other characteristics. At block 204, based on the characteristics of the sample of subterranean rock, select an outcrop rock that suitably models the subterranean rock. Shape the sample of outcrop rock into a rock core having a suitable shape for flow testing. For example, lathe the sample rock to have a 7 inch diameter and cut the sample rock to have a 28 inch axial length. It is understood that the sample rock may be cut to any length and lathed to any diameter that is appropriate. The depth of the perforation expected to be created by the explosive charges of the perforation gun may be used to determine, at least in part, the length of the rock core.

At block 206, perform a high pressure flow test on the rock core. This procedure is described in more detail with reference to FIG. 6A and FIG. 6B described below. In an embodiment, this high pressure flow test involves maintaining an overburden or confining pressure greater than 25000 PSI on the rock core. At block 208, a perforation assembly is coupled to a wellbore facing axial end of the rock core. At block 210, the perforation assembly is activated to perforate the rock core. At block 212. A high pressure flow test is performed on the perforated rock core. In an embodiment, this high pressure flow test involves maintaining an overburden or confining pressure greater than 25000 PSI on the rock core. The high pressure flow test of the perforated rock core may be conducted in substantially the same manner depicted in FIG. 6A or FIG. 6B and described below, with the understanding that the perforation of the metal layer 156 replaces the fast opening of the fast opening flow control device 122, for example the rupture of a rupture disc. In some embodiments, the operations of block 210 and 212 may be considered to be a unified operation. That is, while monitoring the pressure sensed by the second pressure sensor 118, the rock core is perforated while the pressure is periodically sensed by the second pressure sensor 118.

At block 214, based on data collected during the high pressure flow test on the unperforated rock core and during the high pressure flow test on the perforated rock core, determine a production ratio. For example, determine the production ratio based on Eq. 1A or on Eq. 1B above. The processing of block 214 may involve the computer 128 downloading data from the pressure logger 120 and/or from the weight logger 126 and analyzing this data. Alternatively, the data may be streamed from the pressure logger 120 and/or the weight logger 126 as the data is captured by these loggers 120, 126.

The computer 128 may further determine flow rates through the rock core at different times during the high pressure flow test of the unperforated rock core and during the high pressure flow test of the perforated rock core. The flow rates may be determined based on the weight samples downloaded from the weight logger 126 and based on compensating for compression effects of the fluid flowed in the rock core 102. For example, a table that defines fluid compression ratios at different pressures may be referenced by a compensation application executed by the computer 128. A fluid compression ratio may be proportional to the ratio of the volume of a unit mass of the subject fluid at a standard pressure such as atmospheric pressure to the volume of the unit mass of the subject fluid at an elevated pressure, such as at a pressure of 30,000 PSI. Alternatively, the fluid compression ratio may be proportional to the ratio of the volume of a unit mass of the subject fluid at an elevated pressure to the volume of the unit mass of the subject fluid at standard pressure.

The table may define the compression ratio of the subject fluid at each of 5000 PSI, 10000 PSI, 15000 PSI, 20000 PSI, 250000 PSI, 30000 PSI, 35000 PSI, 40000 PSI, 45000 PSI, 50000 PSI, 55000 PSI, and 60000 PSI. In another embodiment, the table may define more or fewer entries. The table may define different pressure indices, for example non-evenly spaced pressure indices. Rather than a table having entries of evenly spaced pressure indices, the table may have entries of evenly spaced compression ratios and corresponding pressure indices associated with each compression ratio. For values of pressure between the table entries, the compression ratio to apply may be linearly interpolated between the two closest pressure indices in the table or interpolated by another method.

At block 216, adapt the perforation gun design based on the production ratio and/or based on other flow metrics determined based on the high pressure flow testing. For example, the shaped charge may be adapted to diffuse explosive energy more broadly, the design of the liner of the shaped charge may be adapted, the tool body proximate to the shaped charge may be adapted. After the perforation gun design is adapted, a second round of core testing may be performed to confirm an improvement in the production ratio associated with the second perforation gun design.

In an embodiment, the rock core 102 may be tested at low pressure, for example under pressure that is less than about 25000 PSI. In an embodiment, the rock core 102 may be tested under pressure of around 5000 PSI or less. A low pressure unperforated flow test may be performed on the rock core 102 before the high pressure unperforated flow test described above and with reference to FIG. 6A and FIG. 6B below. A low pressure perforated flow test may be performed on the rock core 102 after the high pressure perforated flow test described above. Alternatively, the low pressure unperforated and perforated flow tests may be performed on a separate rock core 102 that is separately lathed and cut to the same diameter and length as the rock core 102 used in high pressure flow testing. In this case, the separate rock core 102 may be perforated while subjected to low pressure. During low pressure flow testing, conventional flow sensors may be employed to determine flow rate through the rock core 102 during different times of the test.

The data and analysis of the results of high and low pressure testing may be accumulated and analyzed to determine relationships and/or mappings between high pressure and low pressure rock core test results. Thus, given this mapping, a low pressure core test result may be extrapolated to an estimated high pressure core test result. Alternatively, using this mapping, a high pressure core test result may be extrapolated to an estimated low pressure core test result. This kind of mapping may be determined for different categories of rock as well as for different pressure values. This mapping may be useful in interpreting the results of one type of core testing in the context of the other kind of core testing. For example, perhaps core testing was performed in low pressure testing conditions for a first wellbore and the first wellbore was perforated. A second wellbore in similar rock is core tested in high pressure conditions. A variety of information may be gleaned from the core testing results associated with the first wellbore for use in designing the perforation gun for use in the second wellbore. For example, the mapping may be used to map the first core testing results into the same high pressure environment used for the second testing results and use both those earlier test results and the post-perforation performance of the first wellbore to help design the perforation gun for use in the second wellbore.

Figure 6A:
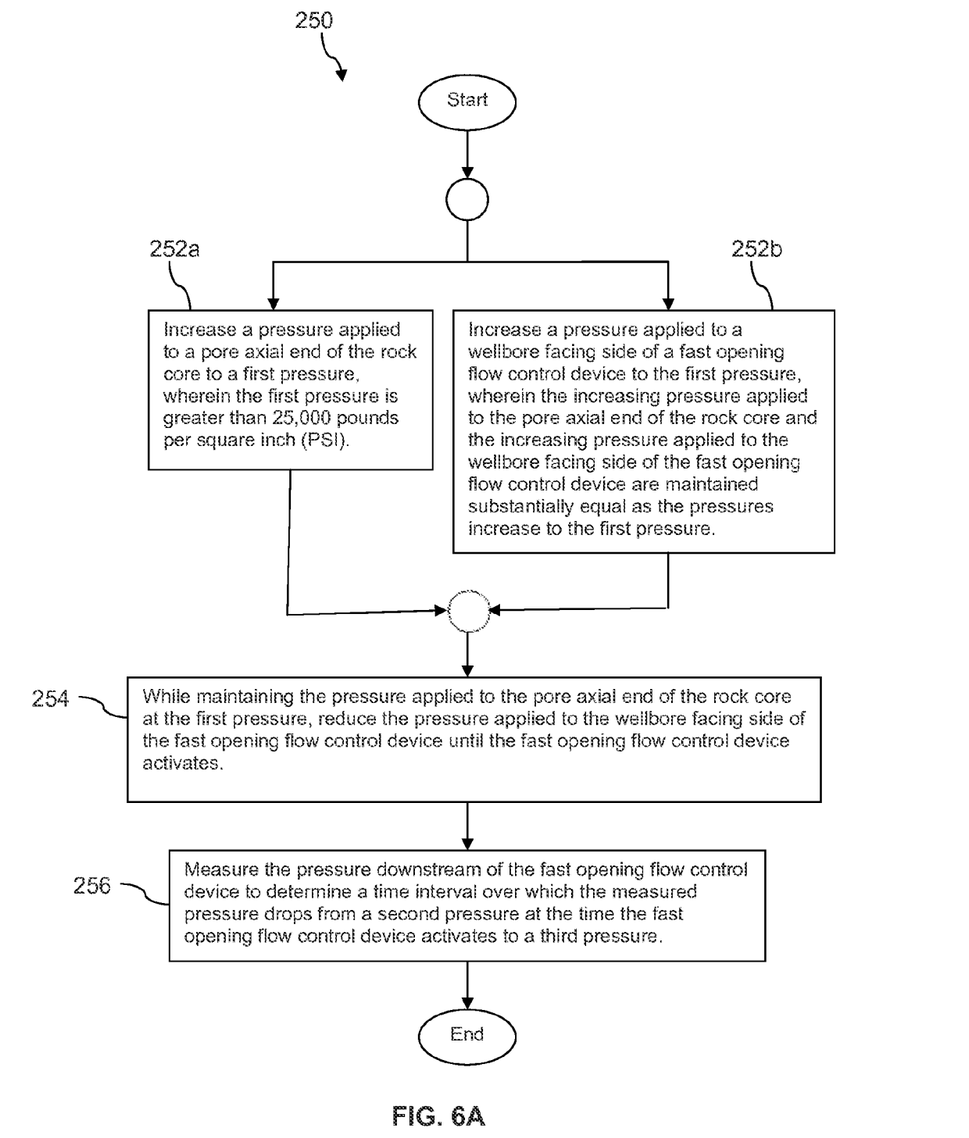
FIG. 6A is a flow chart of another method according to an embodiment of the disclosure.

Turning now to FIG. 6A, a method 250 is described. In an embodiment, the processing of blocks 252a and 252b proceed concurrently. At block 252a, a pressure applied to a pore axial end of the rock core is increased to a first pressure, wherein the first pressure is greater than 25000 PSI. In an exemplary case, the first pressure may be about 40000 PSI. At block 252b, a pressure applied to a wellbore facing side of a fast opening flow control device is increased to the first pressure, where the increasing pressure applied to the pore axial end of the rock core and the increasing pressure applied to the wellbore facing side of the fast opening flow control valve are maintained substantially equal as the pressures increase to the first pressure. In an embodiment, the pressures may be maintained within about 500 PSI of each other during the processing of blocks 252. In an embodiment, an overburden pressure may be applied to the axial surface of the rock core, where the overburden pressure is maintained higher than the pressure on the pore axial end of the rock core.

At block 254, while maintaining the first pressure applied to the pore axial end of the rock core, the pressure applied to the wellbore facing side of the fast opening flow control device is reduced until the fast opening flow control device activates and opens. For example, a pressure differential across a rupture disc causes the rupture disc to open suddenly. At block 256, the pressure on the wellbore side of the fast opening flow control device is measured and/or sensed to determine a time interval over which the measured pressure drops form a second pressure at the time the fast opening flow control valve activates to a third pressure, where the third pressure is less than the second pressure. In an embodiment, the pressure logger 120 may measure the pressures provided by the second pressure sensor 118 that is located on the wellbore side of the fast opening flow control device 122 at a plurality of times, for example periodically. The pressure logger 120 may store this information in a file that is later downloaded by the computer 128. Alternatively, the pressure logger 120 may stream the periodically determined pressure information to the computer 128 at approximately the same time that the pressure measurement or pressure sense value is captured. The computer 128 may determine the time interval over which the pressure drops from the second pressure to the third pressure. This time interval may correspond to the time interval from the initial time 180 to the first end time 180 described above with reference to FIG. 4.

The method 250 may also comprise logging the weight of fluid that flows into the receptacle of the scale 124 after the fast opening flow control device 122 activates. This information may be analyzed, for example by the computer 128, to determine a rate of fluid flow in the rock core 102 at different points in time after the fast opening flow control device 122 activates.

Figure 6B:
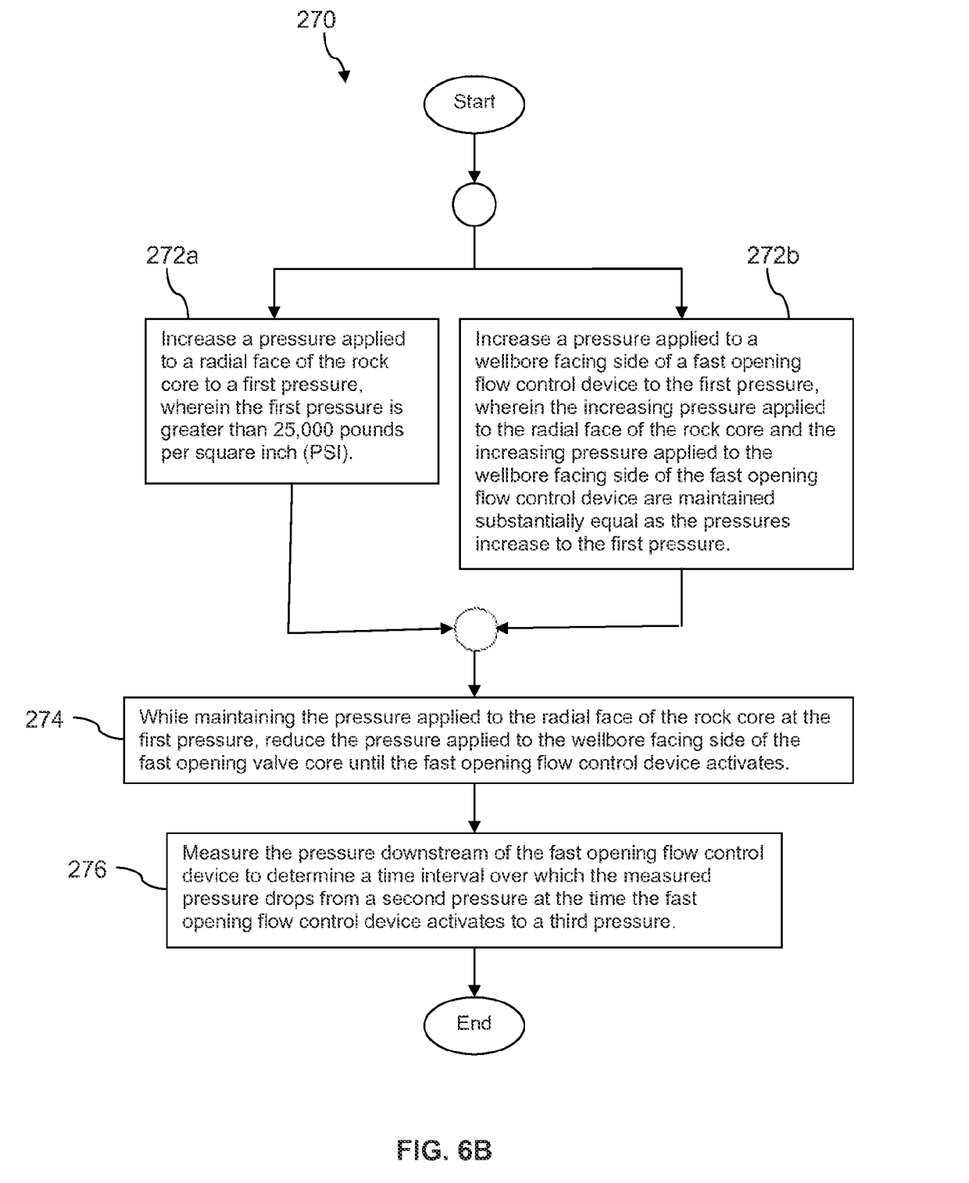
FIG. 6B is a flow chart of another method according to an embodiment of the disclosure.

Turning now to FIG. 6B, a method 270 is described. Method 270 is substantially similar to method 250 described above, with the difference that the pressure that was applied to the pore axial end of the rock core 102 in method 250 is further applied to the radial surface of the rock core 102 in method 270.

In an embodiment, the processing of blocks 272a and 272b proceed concurrently. At block 272a, a pressure applied to a radial face of the rock core 102 is increased to a first pressure, wherein the first pressure is greater than about 25000 PSI. In an embodiment, the pressure may be applied to the pore axial face of the rock core 102 in addition to the radial face of the rock core 102. In an exemplary case, the first pressure may be about 40000 PSI. At block 272b, a pressure applied to a wellbore facing side of a fast opening flow control device is increased to the first pressure, where the increasing pressure applied to the radial face of the rock core and the increasing pressure applied to the wellbore facing side of the fast opening flow control valve are maintained substantially equal as the pressures increase to the first pressure. In an embodiment, the pressures may be maintained within about 500 PSI of each other during the processing of blocks 272.

At block 274, while maintaining the first pressure applied to the radial face of the rock core, the pressure applied to the wellbore facing side of the fast opening flow control device is reduced until the fast opening flow control device activates and opens. For example, a pressure differential across a rupture disc causes the rupture disc to open suddenly. At block 276, the pressure on the wellbore side of the fast opening flow control device is measured and/or sensed to determine a time interval over which the measured pressure drops form a second pressure at the time the fast opening flow control valve activates to a third pressure, where the third pressure is less than the second pressure. In an embodiment, the pressure logger 120 may measure the pressures provided by the second pressure sensor 118 that is located on the wellbore side of the fast opening flow control device 122 at a plurality of times, for example periodically. The pressure logger 120 may store this information in a file that is later downloaded by the computer 128. Alternatively, the pressure logger 120 may stream the periodically determined pressure information to the computer 128 at approximately the same time that the pressure measurement or pressure sense value is captured. The computer 128 may determine the time interval over which the pressure drops from the second pressure to the third pressure. This time interval may correspond to the time interval from the initial time 180 to the first end time 180 described above with reference to FIG. 4.

The method 270 may also comprise logging the weight of fluid that flows into the receptacle of the scale 124 after the fast opening flow control device 122 activates. This information may be analyzed, for example by the computer 128, to determine a rate of fluid flow in the rock core 102 at different points in time after the fast opening flow control device 122 activates.

The information collected during the processing of methods 200 and 250 or 270 may be used to determine the effectiveness of the perforation gun design and to compare among different alternative perforation gun designs.

In an embodiment, the disclosed system and apparatus may be employed to perform a transient pressure test. The method comprises performing a transient pressure test on a first rock core using a first pressure, wherein the first pressure is greater than about 10000 PSI; measuring a first time interval for the pressure sensed at the wellbore axial end of the first rock core to decrease from the first pressure to a second pressure; performing a transient perforation test on a second rock core using the first pressure; measuring a second time interval for the pressure sensed at the wellbore axial end of the second rock core to decrease from the first pressure to a second pressure; and determining a production radio based on the first time interval and the second time interval. It is understood that the first and second rock core are as similar to each other as practicable. For example, the first and second rock core may be lathed and cut to substantially the same form and size. The first and second rock core may be formed from the same type of outcrop rock. Alternatively, in an embodiment, the method can be performed using a single rock core.

Figure 7:
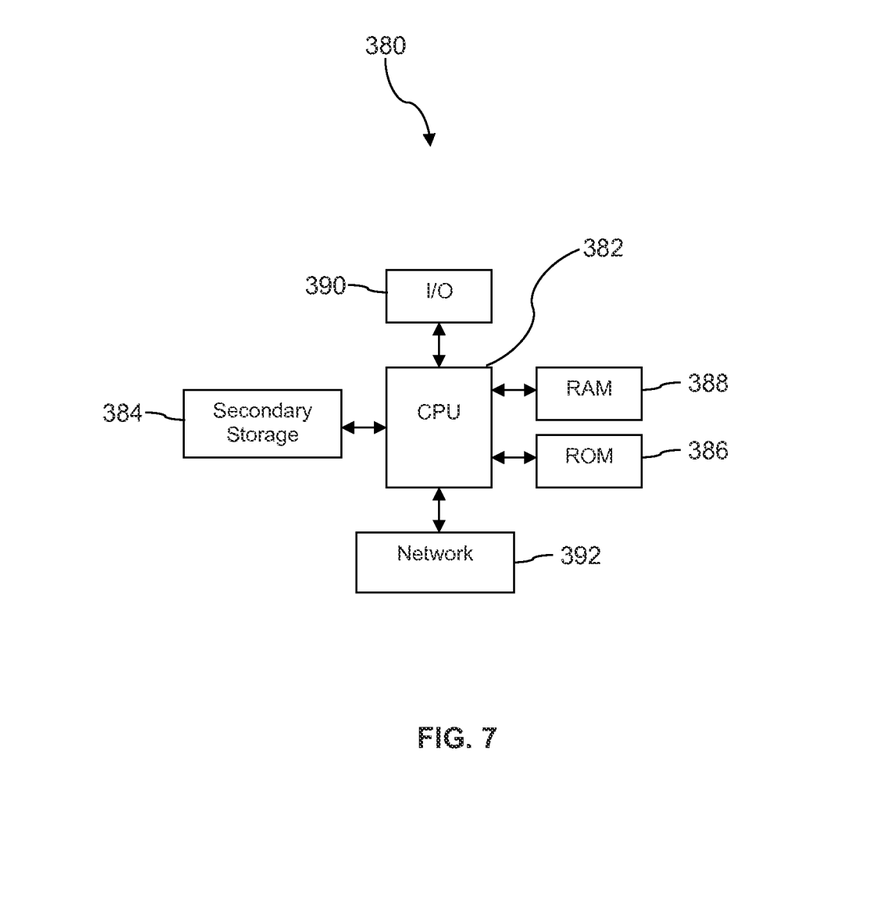
FIG. 7 is an illustration of a computer system according to an embodiment of the disclosure.

FIG. 7 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A rock core flow test system, comprising;
    a first high pressure accumulator coupled to at least one of a pore end of the rock core and a radial surface of the rock core;
    a fast opening flow control device coupled to a wellbore facing end of the rock core, wherein the fast opening flow control device opens when a pressure differential across the fast opening flow control device exceeds a predetermined threshold;
    a second high pressure accumulator coupled to the fast opening flow control device; and
    a pressure sensor coupled to the rock core flow test system between the fast opening flow control device and the second high pressure accumulator.

2. The rock core flow test system of claim 1, wherein the fast opening flow control device is a rupture disc.

3. The rock core flow test system of claim 1, wherein the fast opening high pressure flow control device comprises a shear pin that holds a valve component of the flow control device closed until a shear limit of the shear pin is reached.

4. The rock core flow test system of claim 1, wherein fast opening flow control device is rated for use at pressure of at least about 15,000 pounds per square inch.

5. The rock core flow test system of claim 1, further comprising a fluid overflow collection vessel coupled to a scale.

6. The rock core flow test system of claim 1, further comprising a high speed pressure logging device coupled to the pressure sensor and a weight logging device coupled to the scale, whereby the weight sensed by the scale is periodically logged against time to promote correlating pressure values logged by the high speed pressure logging device to the sensed weight.

7. A method of performing a rock core flow performance test, comprising:
   increasing a pressure applied to a pore axial end of the rock core to a first pressure, wherein the first pressure is greater than about 15,000 pounds per square inch (PSI);
   increasing a pressure applied to a wellbore facing side of a fast opening flow control device to the first pressure, wherein the increasing pressure applied to the pore axial end of the rock core and the increasing pressure applied to the wellbore facing side of the fast opening flow control valve are maintained substantially equal as the pressures increase to the first pressure;
   while maintaining the pressure applied to the pore axial end of the rock core at the first pressure, reducing the pressure applied to the wellbore facing side of the fast opening flow control device until the fast opening flow control device activates, wherein the fast opening flow control device activates in response to a threshold pressure differential across the fast opening flow control device;
   capturing an overflow of a fluid that flows through the rock core after the activation of the fast opening flow control device;
   weighing the overflow of the fluid that flows through the rock core; and
   based on a weight of the overflow of the fluid, determining a first flow volume of the fluid through the rock core.

8. The method of claim 7, wherein the first flow volume is determined at a plurality of time intervals.

9. The method of claim 7, wherein the first flow volume is adjusted based on a compressibility of the fluid and a pressure incident on the fluid inside the rock core.

10. The method of claim 7, wherein the fast opening flow control device comprises a rupture disc.

11. The method of claim 7, wherein the fast opening flow control device comprises a shear pin that holds a valve component of the fast opening flow control device closed until a shear limit of the shear pin is reached.

12. The method of claim 7, wherein the fast opening flow control device activates at a second pressure, and wherein the method further comprises:
   measuring the pressure on a wellbore facing side of the rock core to determine a time interval over which the measured pressure drops from the second pressure to a third pressure; and
   determining a high pressure production ratio of the rock core based on the time interval.

13. The method of claim 12, further comprising selecting a downhole perforation gun design based on the high pressure production ratio.

14. The method of claim 12, further comprising:
   applying a pressure of less than about 5500 pounds per square inch to the pore axial end of the rock core; and
   determining a low pressure production ratio of the rock core based on applying the pressure of less than about 5500 pounds per square inch to the pore axial end of the rock core.

15. The method of claim 14, further comprising:
   determining a correlation between the high pressure production ratio and the low pressure production ratio of a plurality of rock cores; and
   based on the correlation, estimating a high pressure production ratio of a rock core based on a low pressure production ratio determined by a low pressure test.

16. The method of claim 15, wherein the correlation is further based on at least one of a type of rock core and a permeability of rock core.

17. The method of claim 7, further comprising applying an overburden pressure radially to the rock core, wherein the overburden pressure exceeds the first pressure.

18. The method of claim 17, further comprising:
   adhering a cap to the wellbore facing axial end of the rock core; and
   perforating the cap and the rock core with an explosive charge.

19. The method of claim 18, further comprising:
   capturing an overflow of fluid that flows through the rock core after perforating the cap;
   weighing the overflow of the fluid that flows through the rock core after perforating the cap; and
   based on the weight of the overflow of the fluid that flows through the rock core after perforating the cap, determining a second flow volume of the fluid through the rock core after perforating the cap.

20. The method of claim 19, further comprising selecting a perforation gun design based on the first flow volume and the second flow volume.

\* \* \* \* \*